US00PP37457P2

(12) United States Plant Patent
Gómez Alvarado

(10) Patent No.: US PP37,457 P2
(45) Date of Patent: Jun. 9, 2026

(54) BLACKBERRY PLANT NAMED 'AGV-22'

(50) Latin Name: ***Rubus subgenus Eubatus* sect. Moriferi & Ursini**
Varietal Denomination: AGV-22

(71) Applicant: AGV Innovation & Varieties LLC, Los Angeles, CA (US)

(72) Inventor: Héctor Uri Gómez Alvarado, Techaluta de Montenegro Techal (MX)

(73) Assignee: AGV Innovation & Varieties LLC, Los Angeles, CA (US)

( * ) Notice: Subject to any disclaimer, the term of this patent is extended or adjusted under 35 U.S.C. 154(b) by 0 days.

(21) Appl. No.: 19/204,284

(22) Filed: May 9, 2025

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

PP26,413 P3 * 2/2016 Ortiz ..... A01H 6/7499 Plt./203

* cited by examiner

*Primary Examiner* — Susan McCormick Ewoldt
*Assistant Examiner* — Zachariah Allan Kay
(74) *Attorney, Agent, or Firm* — Hunt IP Law

(57) ABSTRACT

The new and distinct variety of blackberry plant 'AGV-22' is provided. The variety can be distinguished by its outstanding features of crunchy and sweet fruit, fruit with long shelf life, high firmness, and low regression.

6 Drawing Sheets

Latin name of the genus and species:

Botanical classification: a. Genus—*Rubus* subgenus *Eubatus* sect. Moriferi & Ursini.

Variety denomination: The new blackberry plant claimed is of the variety denominated 'AGV-22'.

CROSS REFERENCE TO RELATED APPLICATIONS

The application claims benefit under 35 USC § 119 to Mexican Plant Breeder's Right Registration Application No. MX_4534_NLI published on Apr. 18, 2024, for a blackberry plant with a variety denomination of 'AGV-22', which is herein incorporated by reference in its entirety.

SUMMARY

The present invention relates to a new and distinct variety of blackberry, which has been given the variety denomination of 'AGV-22'.

The new blackberry variety is a selection resulting from a sexual cross of blackberry plants in high tunnels/hoop houses at Los Reyes, Michoacán, Mexico in 2015, involving a seed parent known as 'BG-36' (unpatented) and a pollen parent known as 'BG-52' (unpatented).

The selection was subsequently evaluated for 3 years at Los Reyes, Michoacán, Mexico and 2 years at Techaluta de Montenegro, Jalisco, Mexico.

Asexual reproduction of the new variety by root cutting propagation since 2017 at Los Reyes, Michoacán, Mexico has demonstrated that the new variety reproduces true to type with all of the morphological characteristics, as herein described, firmly fixed and retained through successive generations of such asexual propagation.

Selection criteria were fruiting primocane with fruit quality that has high firmness, sweet flavor (18° Bx) and low acidity (0.9 to 1.1 rate acidity—measured by ATAGO PAL-BX/ACID F5 (Multi-fruits) tool), high productivity, vigorous plants characterized by plants that grow easily in the spring and summer with an average of 2.4 cm per day, and resistance to pests and diseases.

Compared to its parents 'AGV-22' shows great expression of heterozygosity because it is more resistant than its parents to fungal pathogens. Unlike its parents, 'AGV-22' is highly resistant to *Fusarium* or *Peronospora*. Unlike its parents, 'AGV-22' is resistant to two-spotted spider mite (*Tetranychus urtichae*), and to redberry mite (*Acalitus essigi*). Compared to 'Tupi', 'AGV-22' is much more resistant to regression of fruit, and more resistant to fungal diseases like *Fusarium*. 'Tupi' and 'AGV-22' are similar in terms of resistance to other plagues.

The following characteristics of the new variety have been repeatedly observed and can be used to distinguish 'AGV-22' as a new and distinct variety of blackberry plant: crunchy and sweet fruit, fruit with long shelf life, high firmness, and low regression. 'AGV-22' demonstrates fruit firmness that is high enough to avoid leaking once the fruit is packaged and to create a crunchy experience when eaten. Its shelf life is about 17 days, the sweetness capacity is 18° Bx, and acidity rate is 0.9 to 1.1 (measured by ATAGO PAL-BX/ACID F5 (Multi-fruits) tool).

PHOTOGRAPHS

The accompanying photographic illustrations show the typical appearance of the new variety 'AGV-22'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
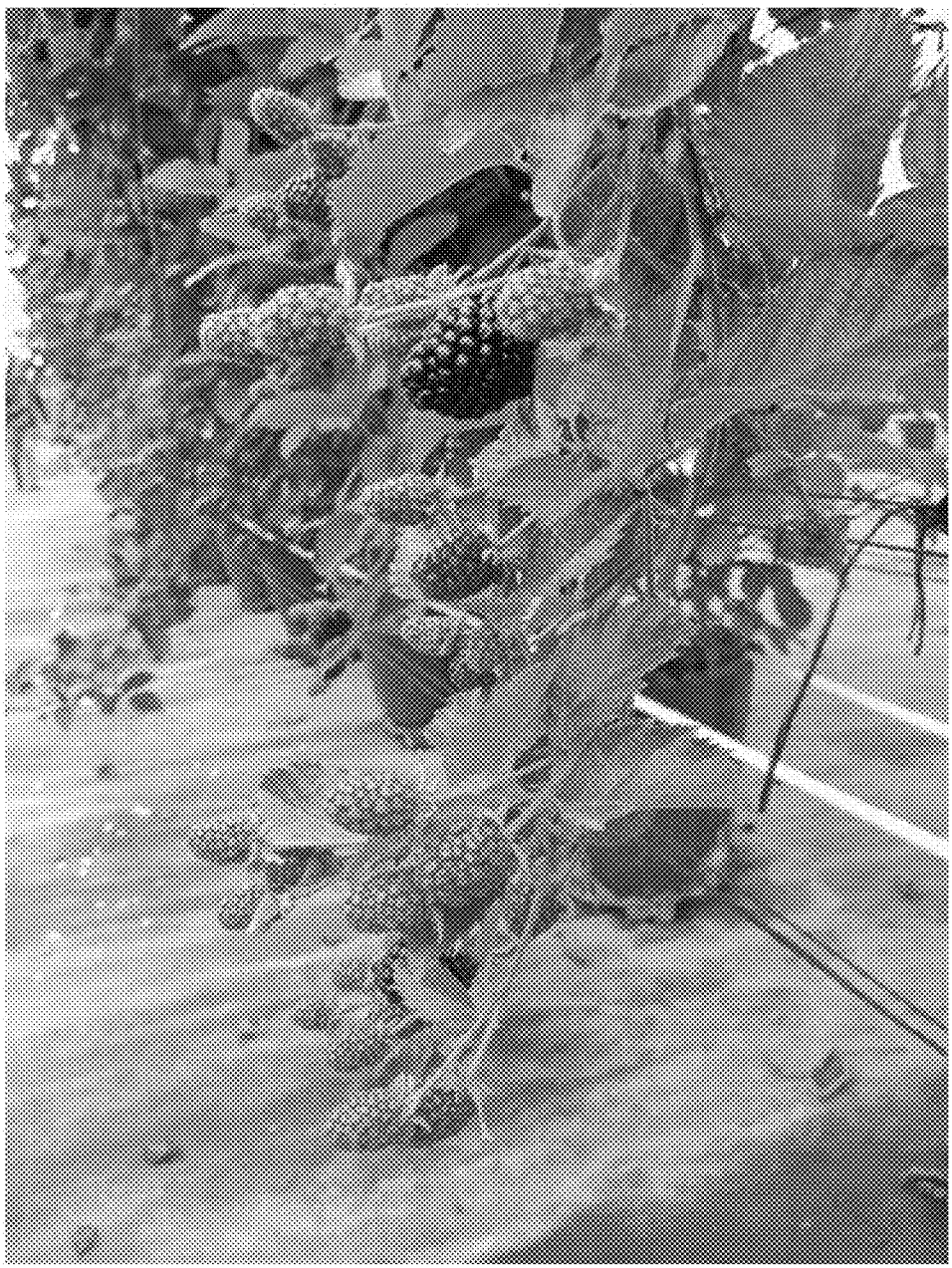
FIG. 1 is a photograph of the new variety, demonstrating immature fruit.
Figure 2:
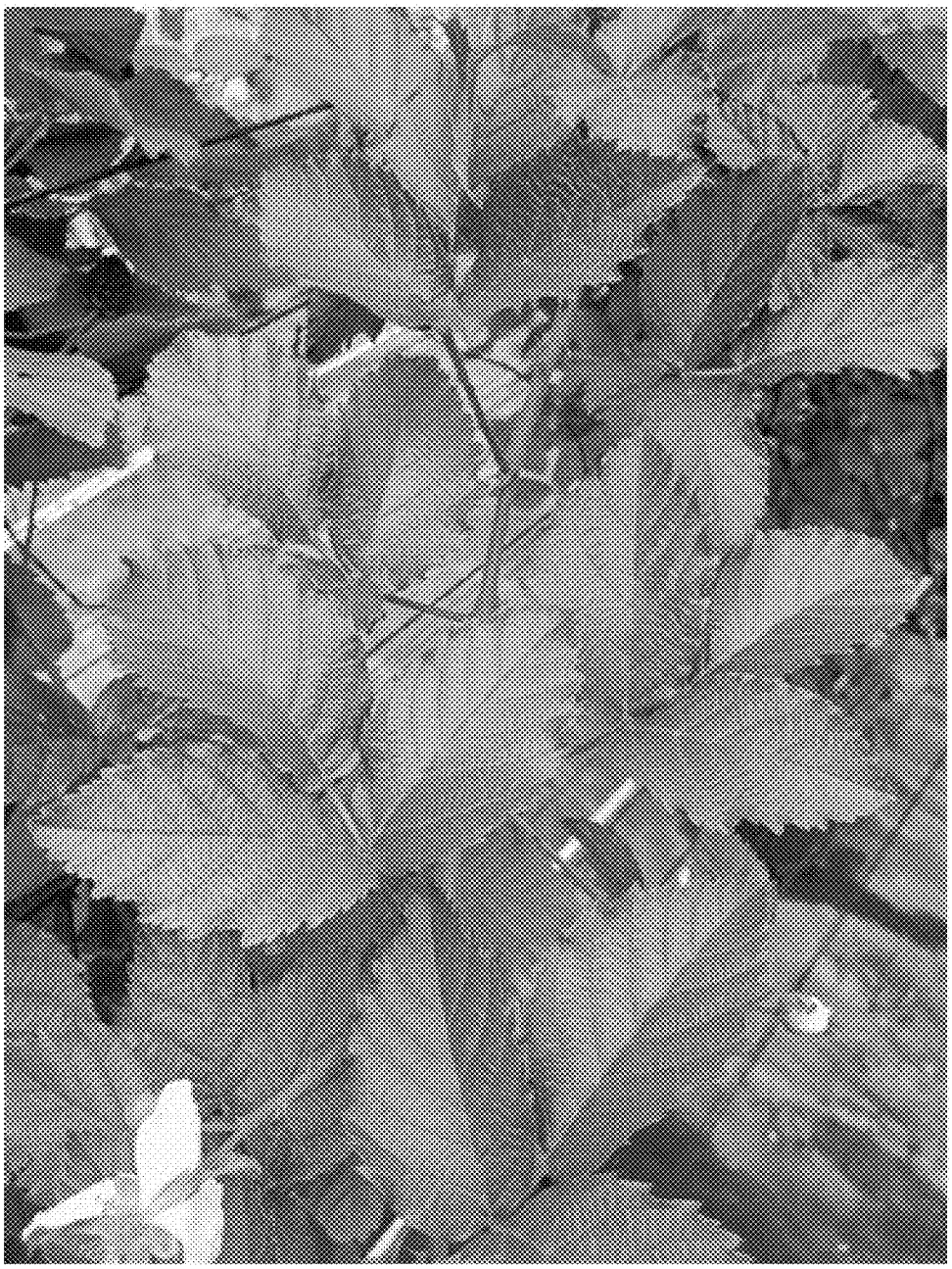
FIG. 2 is a photograph of the new variety, demonstrating leaves.
Figure 3:
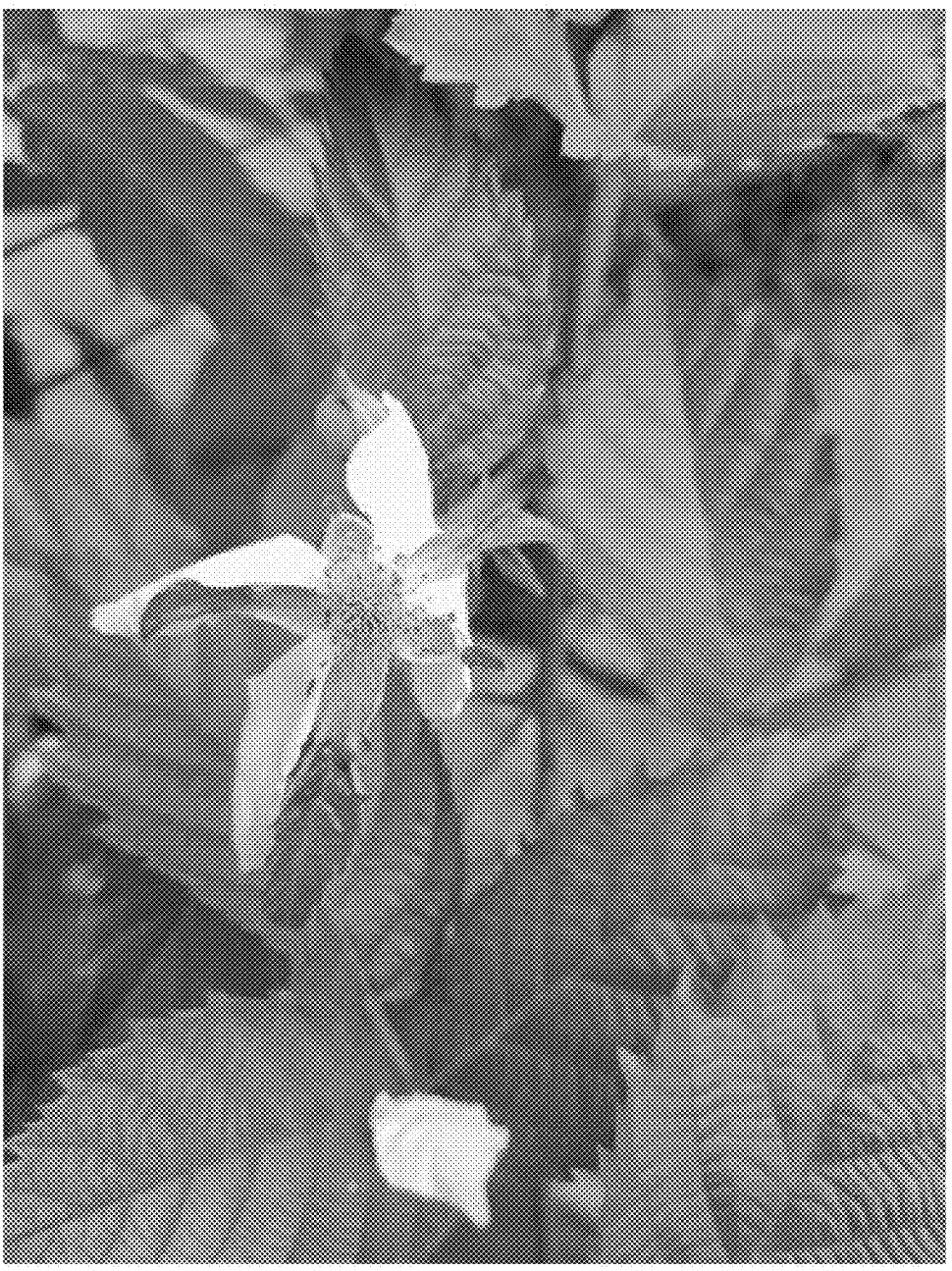
FIG. 3 is a photograph of the new variety, demonstrating leaves and flowers.
Figure 4:
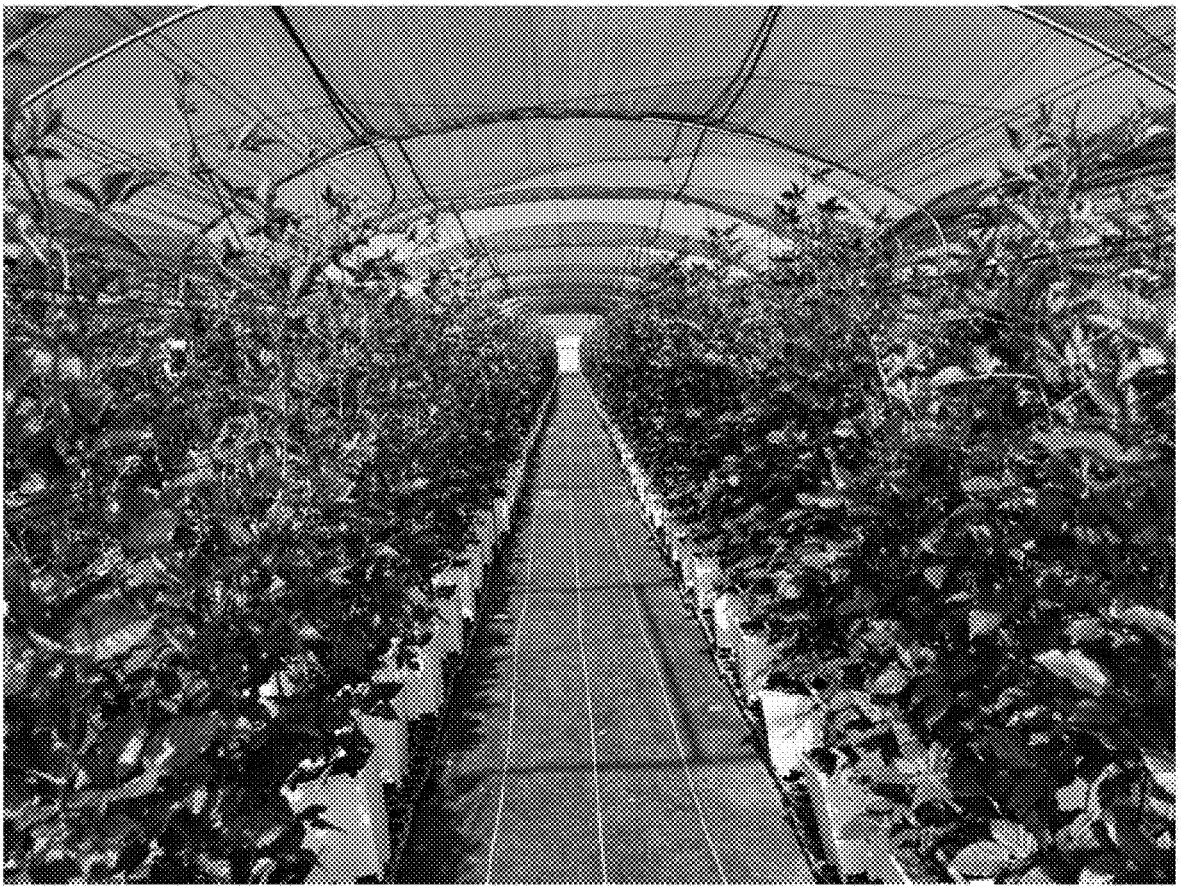
FIG. 4 is a photograph of the new variety, demonstrating semi-erect growth habit.
Figure 5:
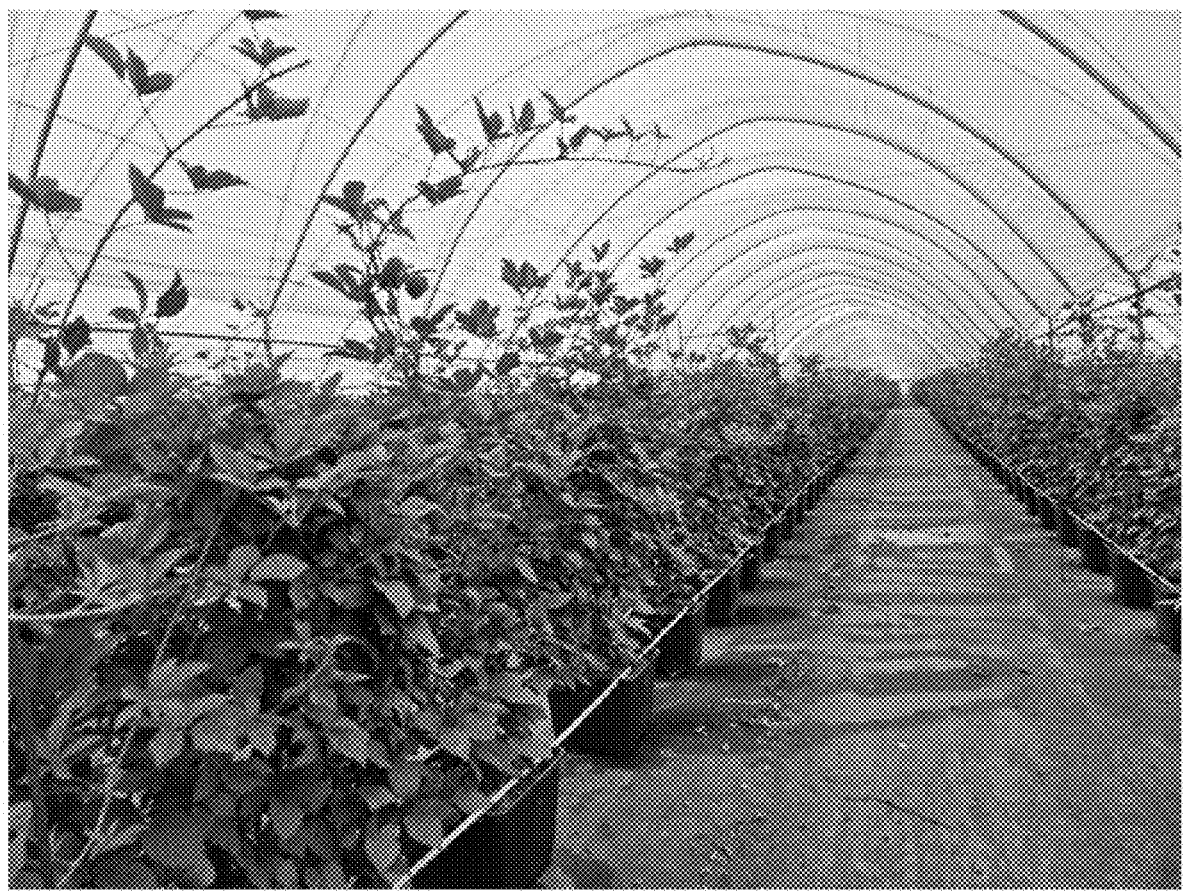
FIG. 5 is a photograph of the new variety, demonstrating semi-erect growth habit.
Figure 6:
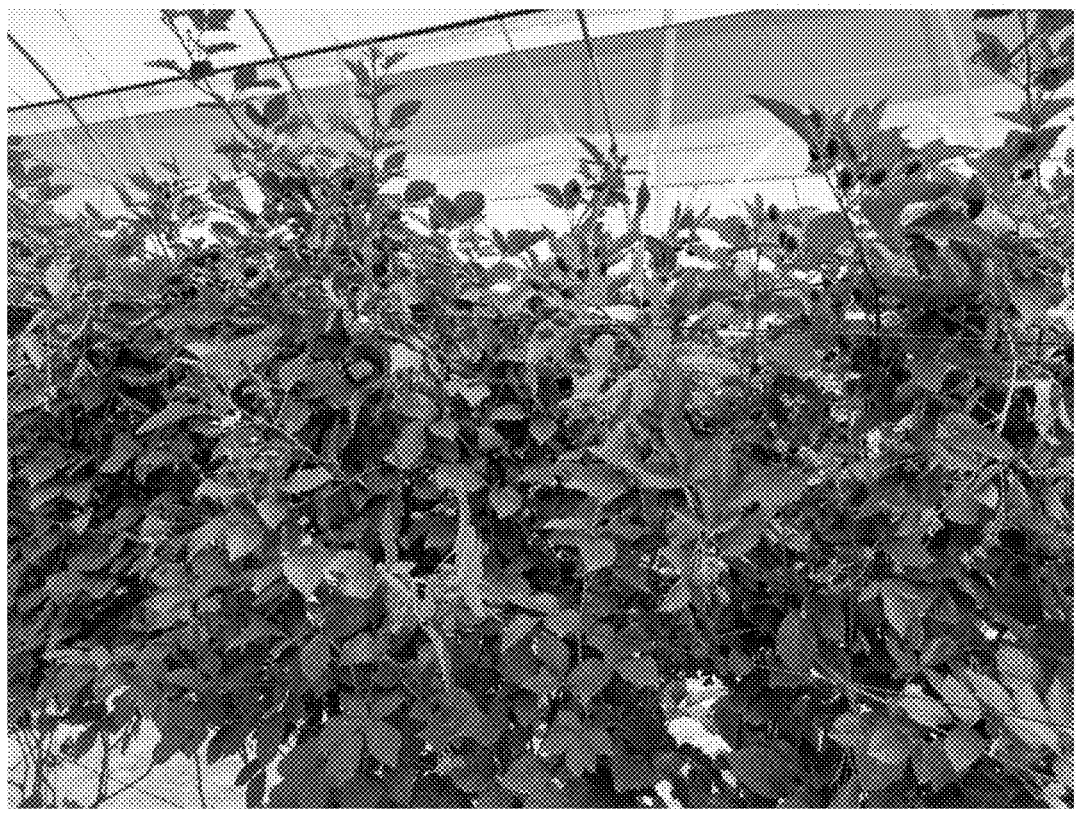
FIG. 6 is a photograph of the new variety, demonstrating leaves and immature fruit.

The following detailed description sets forth the distinctive characteristics of 'AGV-22'. The datum which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in Techaluta de Montenegro Jalisco, Mexico. Color notations are in reference to the standard R.H.S. Colour Chart, 6th edition (2015), known to those of ordinary skill in the art.

Classification:

b. *Family*.—Rosaceae.

c. *Botanical*.—*Rubus* subgenus *Eubatus* sect. Moriferi & Ursini.

d. *Common name*.—Blackberry.

e. *Variety name*.—'AGV-22'.

Parentage:

f. *Female parent*.—'BG-36' (unpatented).

g. *Male parent*.—'BG-52' (unpatented).

PLANT

General:

h. *Vigor*.—Medium. Average growth is 2.4 cm per day (vegetative stage). Less vigorous than 'Tupi'.

i. *Growth habit*.—Bush semi-erect.

j. *Propagation*.—Root cuttings.

k. *Self-fruitfulness*.—Yes.

l. *Time of bud burst*.—Autumn.

m. *Height*.—1.8-2 m.

n. *Width*.—1-1.2 m.

o. *Length/width ratio*.—1:1.8.

p. *Primocane* (*current year's cane*).—i. Color — Green. ii. Cane length in autumn — 1.8-2 m. iii. Internodal distance at central ⅓ of cane — 5-7 cm. iv. Anthocyanin coloration of cane — RHS: 79A. v. Cane bloom — Absent. vi. Time of caneqj emergence — Autumn.

q. *Very young shoot*.—vii. Anthocyanin coloration of apex during rapid growth — RHS: 59A.

r. *Floricane* (*previous year's cane*).—viii. Dormant cane color — Green. ix. Fruiting lateral attitude — Semi-erect. x. Fruiting lateral length — 40-60 cm.

s. *Prickles*.—xi. Presence — Present. xii. Density — Low-medium. Fewer prickles than 'Tupi'. xiii. Length at 1 inch in height at end of harvest (from base to tip) — 7 mm. xiv. Color — RHS: 144C.

CANES

General:

t. *Fruiting lateral length*.—50-80 cm.

u. *Number of fruit per lateral*.—11-21.

v. *Fruiting on current year's cane*.—Present.

w. *Cane internodal distance*.—8-14 cm.

x. *Number of new canes during flowering*.—1-2.

y. *Glaucosity*.—Present.

z. *Young shoots*.—i. Quantity — 4-6. ii. Time of emergence from soil — 45 days. iii. Anthocyanin coloration (during rapid growth) — RHS: 59A. iv. Intensity of green color — High, RHS: 135A. v. Number of glandular hairs — Absent.

aa. *Dormant cane*.—i. Length — 50-60 cm. ii. Diameter (in central third) — 3 mm. iii. Cross section (from mid cane observed at end of first growing season) — Rounded. iv. Number of branches — 40-50. v. Distribution of branches — Over whole length. vi. Anthocyanin coloration — Present. vii. Prickles — Present.

LEAVES

General:

bb. *Type*.—Pinnate.

cc. *Predominant number of leaflets*.—5.

dd. *Profile of leaflets in cross section*.—90°.

ee. *Leaf rugosity*.—Present.

ff. *Overlapping or relative position of lateral leaflet*.—Overlapping.

gg. *Color*.—i. Upper surface — RHS: 137A. ii. Lower surface — RHS: 138B.

hh. *Surface texture of upper side*.—Rough.

ii. *Surface texture of lower side*.—Rough.

jj. *Glossiness of upper side*.—Present.

kk. *Cross section profile*.—Convex.

ll. *Leaflets*.—i. Shape — Elliptic. ii. Margin — Serrate. iii. Depth of incisions — Medium, similar to 'Tupi'. iv. Type of incision margin — Serrate. v. Apex — Apiculate. vi. Base — Rounded. vii. Rachis length between terminal leaflet and adjacent lateral leaflet — 1.5-3.3 cm.

mm. *Lateral leaflet* (*basal pair*).—i. Length — 9-11 cm. ii. Width — 5-8 cm. iii. Length/width ratio — 1:1.5. iv. Relative position of lateral leaflets — Transversal to the last one. v. Margin — Serrate. vi. Overall shape — Elliptic. vii. Apex shape — Apiculate. viii. Base shape — Rounded.

nn. *Terminal leaflet*.—i. Length — 5-6 cm. ii. Width — 3-4 cm. iii. Length/width ratio — 1:1.5. iv. Lobing — Absent. v. Undulation of margin (rippling of margin) — Present. vi. Blistering between veins (rugosity) — Present. vii. Shape — Elliptic. viii. Apex — Apiculate. ix. Base — Acute. x. Margin — Serrate. xi. Cross-section — V-shaped.

oo. *Petiole*.—i. Diameter — 1.5-2 mm. ii. Pigmentation — i. Upper surface — Green. ii. Lower surface — Green reddish.

pp. *Stipule*.—i. Size — 3 mm-18 mm. ii. Orientation — Erect.

qq. *Color*.—RHS: 144A.

FLOWER rr. *Flower diameter*.—3-6 cm.

ss. *Flower number* (*at* 3$^{rd}$ *noted from tip of lateral*).—4-5 per charger.

tt. *Petal*.—i. Length — 2-2.5 cm. ii. Width — 1.5-1.8 cm. iii. Length/width — 1:1.5. iv. Color of upper side — White. v. Color of lower side — White.

uu. *Pedicel*.—i. Length — 3-4 cm. ii. Diameter — 1-2 mm vv. *Time of beginning of flowering on previous year's cane*.—94 days.

ww. *Time of beginning of flowering on current year's cane*.—106 days.

xx. *Sepal*.—i. Length — 0.6-0.8 cm. ii. Width — 0.6 cm. iii. Shape — Conic. iv. Color — Light green.

yy. *Pedicel*.—i. Length — 2-3 cm. ii. Diameter — 1-1.5 mm. iii. Color — Green. iv. Surface texture — Smooth.

zz. *Peduncle*.—i. Color — Green. ii. Anthocyanin coloration — Very weak. iii. Surface texture — Smooth.

FRUIT

General:

aaa. *Size*.—Medium.

bbb. *Length*.—3-4 cm.

ccc. *Width*.—1.5-2 cm.

ddd. *Ratio of length to width*.—2:1.

eee. *General shape in lateral view*.—Conic.

fff. *Weight* (*g/fruit*).—8.5-9.8 g.

ggg. *Soluble solids* (%) (*in Brix*).—11.

hhh. *Titratable acidity* (% *as citric acid*).—1.0.

iii. *Seed weight* (*g/seed*).—0.004 g.

jjj. *Number of drupelets/fruit*.—94-100 average.

kkk. *Size of drupelet*.—Medium.

lll. *Color*.—i. Immature — RHS: 143A. ii. Maturing — RHS: 183A. iii. Mature — RHS: 202A.

mmm. *Firmness*.—High.

nnn. *Glossiness*.—Medium.

ooo. *Shape in longitudinal section*.—Ovate.

ppp. *Time of ripening on previous year's cane*.—50-60 days.

qqq. *Time of ripening on current year's cane*.—50-60 days.

rrr. *Harvest interval*.—3 to 4 days.

sss. *Yield*.—Medium.

SEED

General:

ttt. *Length*.—4 mm.

uuu. *Width*.—3 mm.

vvv. *Shape*.—Semi-spheroid.

www. *Color*.—Yellow.

PRODUCTION

General:

rrr. *Main bearing type*.—Primocane.

sss. *Primocane* (*current year's cane*).—i. Time of beginning of flowering — May to August. ii. Time of beginning of fruit ripening — August. iii. Length of fruiting period — September to January. iv. Yield — 18 tons/hectare.

ttt. *Floricane* (*previous year's cane*).—i. Time of vegetative bud burst — April to July. ii. Time of beginning of flowering — July to September. iii. Time of beginning of fruit ripening — September to October. iv. Length of fruiting period — October to March. v. Yield — 11 tons/hectare.

RESISTANCE TO DISEASES, PESTS, AND ABIOTIC STRESS

General:

xxx. *Fruit storage life and shipping quality*.—Good. Average of 17 days shelf life.

yyy. *Market use*.—Retail.

zzz. *Plant/fruit disease and pest resistance/susceptibility*.—i. Redberry mite (*Acalitus essigi*) — Resistant. ii. Two-spotted spider mite (*Tetranychus urticae*) — Resistant. iii. *Fusarium* fungus (*Fusarium* spp) — Highly resistant. iv. Downy mildew (*Peronospora sparsa*) — Highly resistant.

aaaa. *Cold hardiness*.—Tested at Guadalajara Jalisco — USDA 10a, and Camalú Baja California Norte — USDA 10b.

The invention claimed is:

1. A new and distinct variety of blackberry named 'AGV-22', as illustrated and described herein.

* * * * *